United States Patent
Cabiri et al.

(10) Patent No.: US 9,656,019 B2
(45) Date of Patent: May 23, 2017

(54) APPARATUSES FOR SECURING COMPONENTS OF A DRUG DELIVERY SYSTEM DURING TRANSPORT AND METHODS OF USING SAME

(71) Applicant: MEDIMOP Medical Projects Ltd., Ra'anana (IL)

(72) Inventors: Oz Cabiri, Macabim-Reut (IL); Reuven Y. Filman, Netanya (IL); Yossi Bar-El, Beit Arye (IL)

(73) Assignee: MEDIMOP MEDICAL PROJECTS LTD., Ra'Anana (IL)

( * ) Notice: Subject to any disclaimer, the term of this patent is extended or adjusted under 35 U.S.C. 154(b) by 802 days.

(21) Appl. No.: 13/874,017

(22) Filed: Apr. 30, 2013

(65) Prior Publication Data

US 2013/0245596 A1    Sep. 19, 2013

Related U.S. Application Data

(63) Continuation-in-part of application No. 12/244,666, filed on Oct. 2, 2008, now Pat. No. 9,173,997, and a
(Continued)

(51) Int. Cl.
*A61M 5/145* (2006.01)
*A61M 5/142* (2006.01)
(Continued)

(52) U.S. Cl.
CPC ...... *A61M 5/1452* (2013.01); *A61M 5/14248* (2013.01); *A61M 5/14566* (2013.01);
(Continued)

(58) Field of Classification Search
CPC .......... A61M 5/14566; A61M 5/14248; A61M 5/1452; A61M 2005/1426; A61M 5/1413;
(Continued)

(56) References Cited

U.S. PATENT DOCUMENTS

| 232,432 A | * 9/1880 | Allison ................. F16L 15/004 |
| | | 285/114 |
| 1,795,630 A | 3/1931 | Wilson |

(Continued)

FOREIGN PATENT DOCUMENTS

| CN | 1747683 A | 3/2006 |
| CN | 1863566 A | 11/2006 |

(Continued)

OTHER PUBLICATIONS

Office Action issued Oct. 9, 2013 in IL Application No. 208634.
(Continued)

*Primary Examiner* — Theodore Stigell
(74) *Attorney, Agent, or Firm* — Panitch Schwarze Belisario & Nadel LLP

(57) ABSTRACT

An assembly of a drug delivery system, comprising: a first component; a second component which is configured to move linearly with respect to the first component; and, a resistance element configured to resist linear movement during transport of the first component with respect to the second component in a closed transport configuration but which is adapted to be overcome during nominal operation of the drug delivery system.

11 Claims, 8 Drawing Sheets

Related U.S. Application Data continuation-in-part of application No. 13/521,181, filed as application No. PCT/US2011/021605 on Jan. 19, 2011, now Pat. No. 9,259,532, which is a continuation of application No. 12/689,250, filed on Jan. 19, 2010, now Pat. No. 7,967,795.

(60) Provisional application No. 60/997,459, filed on Oct. 2, 2007.

(51) Int. Cl.
   *A61M 5/14* (2006.01)
   *A61M 5/168* (2006.01)
   *A61M 5/172* (2006.01)
   *A61M 5/315* (2006.01)

(52) U.S. Cl.
   CPC ....... *A61M 5/1413* (2013.01); *A61M 5/16827* (2013.01); *A61M 5/1723* (2013.01); *A61M 2005/1426* (2013.01); *A61M 2005/14252* (2013.01); *A61M 2005/14268* (2013.01); *A61M 2005/31518* (2013.01); *A61M 2205/3523* (2013.01); *A61M 2205/3569* (2013.01); *Y10T 29/49826* (2015.01)

(58) Field of Classification Search
   CPC ............ A61M 5/16827; A61M 5/1723; A61M 2005/3158; A61M 2205/3569; A61M 2005/14252; A61M 2005/14268; A61M 2205/3523
   USPC .......................................................... 411/436
   See application file for complete search history.

(56) References Cited

U.S. PATENT DOCUMENTS

| | | |
|---|---|---|
| 2,677,373 A | 5/1954 | Barradas |
| 2,702,547 A | 2/1955 | Glass |
| 2,860,635 A | 11/1958 | Wilburn |
| 3,203,269 A | 8/1965 | Perrine |
| 3,212,685 A * | 10/1965 | Swan ...................... A61M 3/00 222/386 |
| 3,623,474 A | 11/1971 | Heilman et al. |
| 3,794,028 A | 2/1974 | Mueller et al. |
| 3,994,295 A | 11/1976 | Wulff |
| 4,195,636 A | 4/1980 | Behnke |
| 4,218,724 A | 8/1980 | Kaufman |
| 4,273,122 A | 6/1981 | Whitney et al. |
| 4,300,554 A | 11/1981 | Hessberg et al. |
| 4,403,987 A | 9/1983 | Gottinger |
| 4,435,173 A | 3/1984 | Siposs et al. |
| 4,465,478 A | 8/1984 | Sabelman et al. |
| 4,564,054 A | 1/1986 | Gustavsson |
| 4,565,543 A | 1/1986 | Bekkering et al. |
| 4,585,439 A | 4/1986 | Michel |
| 4,599,082 A | 7/1986 | Grimard |
| 4,601,702 A | 7/1986 | Hudson |
| 4,664,654 A | 5/1987 | Strauss |
| 4,685,903 A | 8/1987 | Cable et al. |
| 4,698,055 A | 10/1987 | Sealfon |
| 4,735,311 A | 4/1988 | Lowe et al. |
| 4,810,215 A | 3/1989 | Kaneko |
| 4,850,966 A | 7/1989 | Grau et al. |
| 4,867,743 A | 9/1989 | Vaillancourt |
| 4,886,499 A | 12/1989 | Cirelli et al. |
| 4,892,521 A | 1/1990 | Laico et al. |
| 4,919,596 A | 4/1990 | Slate et al. |
| 4,929,241 A | 5/1990 | Kulli |
| 4,950,246 A | 8/1990 | Muller |
| 4,964,866 A | 10/1990 | Szwarc |
| 5,051,109 A | 9/1991 | Simon |
| D322,671 S | 12/1991 | Szwarc |
| 5,109,850 A | 5/1992 | Blanco et al. |
| 5,112,317 A | 5/1992 | Michel |
| 5,131,816 A | 7/1992 | Brown et al. |
| 5,190,521 A | 3/1993 | Hubbard et al. |
| 5,254,096 A | 10/1993 | Rondelet et al. |
| 5,300,045 A | 4/1994 | Plassche, Jr. |
| 5,318,522 A | 6/1994 | D'Antonio |
| 5,342,313 A | 8/1994 | Campbell et al. |
| 5,348,544 A | 9/1994 | Sweeney et al. |
| 5,366,498 A | 11/1994 | Brannan et al. |
| 5,383,865 A | 1/1995 | Michel |
| 5,478,315 A | 12/1995 | Brothers et al. |
| 5,482,446 A | 1/1996 | Williamson et al. |
| 5,496,274 A | 3/1996 | Graves et al. |
| 5,501,665 A | 3/1996 | Jhuboo et al. |
| 5,505,709 A | 4/1996 | Funderburk et al. |
| 5,562,624 A | 10/1996 | Righi et al. |
| 5,562,686 A | 10/1996 | Sauer et al. |
| 5,593,390 A | 1/1997 | Castellano et al. |
| 5,616,132 A | 4/1997 | Newman |
| 5,624,400 A | 4/1997 | Firth et al. |
| 5,643,218 A | 7/1997 | Lynn et al. |
| 5,645,530 A | 7/1997 | Boukhny et al. |
| 5,645,955 A | 7/1997 | Maglica |
| 5,647,853 A | 7/1997 | Feldmann et al. |
| 5,658,256 A | 8/1997 | Shields |
| 5,662,678 A | 9/1997 | Macklin |
| 5,672,160 A | 9/1997 | Osterlind et al. |
| 5,690,618 A | 11/1997 | Smith et al. |
| 5,728,075 A | 3/1998 | Levander |
| D393,314 S | 4/1998 | Meisner et al. |
| 5,766,186 A | 6/1998 | Faraz et al. |
| 5,795,675 A | 8/1998 | Maglica |
| 5,800,420 A | 9/1998 | Gross et al. |
| 5,807,375 A | 9/1998 | Gross et al. |
| 5,810,784 A | 9/1998 | Tamaro |
| 5,814,020 A | 9/1998 | Gross |
| 5,836,920 A | 11/1998 | Robertson |
| 5,848,991 A | 12/1998 | Gross et al. |
| 5,851,197 A | 12/1998 | Marano et al. |
| 5,858,001 A * | 1/1999 | Tsals ................. A61M 5/14248 604/135 |
| 5,858,008 A | 1/1999 | Capaccio |
| 5,868,710 A | 2/1999 | Battiato et al. |
| 5,893,842 A | 4/1999 | Imbert |
| 5,894,015 A | 4/1999 | Rechtin |
| 5,926,596 A | 7/1999 | Edwards et al. |
| 5,931,814 A | 8/1999 | Alex et al. |
| 5,941,850 A | 8/1999 | Shah et al. |
| 5,944,699 A | 8/1999 | Barrelle et al. |
| 5,948,392 A | 9/1999 | Haslwanter et al. |
| 5,954,697 A | 9/1999 | Srisathapat et al. |
| 5,957,895 A | 9/1999 | Sage et al. |
| 5,968,011 A | 10/1999 | Larsen et al. |
| 5,993,423 A | 11/1999 | Choi |
| 6,004,297 A | 12/1999 | Steenfeldt-Jensen et al. |
| 6,033,245 A | 3/2000 | Yamkovoy |
| 6,033,377 A | 3/2000 | Rasmussen et al. |
| 6,064,797 A | 5/2000 | Crittendon et al. |
| 6,074,369 A | 6/2000 | Sage et al. |
| 6,186,982 B1 | 2/2001 | Gross et al. |
| 6,200,289 B1 | 3/2001 | Hochman et al. |
| 6,200,296 B1 | 3/2001 | Dibiasi et al. |
| 6,224,569 B1 | 5/2001 | Brimhall |
| 6,248,093 B1 | 6/2001 | Moberg |
| 6,270,481 B1 | 8/2001 | Mason et al. |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,293,925 B1 | 9/2001 | Safabash et al. |
| 6,302,633 B1 | 10/2001 | Poe |
| 6,336,729 B1 | 1/2002 | Pavelle et al. |
| 6,345,968 B1 | 2/2002 | Shupe |
| 6,377,848 B1 | 4/2002 | Garde et al. |
| 6,391,005 B1 | 5/2002 | Lum et al. |
| 6,423,029 B1 | 7/2002 | Elsberry |
| D465,026 S | 10/2002 | May et al. |
| 6,458,102 B1 | 10/2002 | Mann et al. |
| 6,485,461 B1 | 11/2002 | Mason et al. |

(56) References Cited

U.S. PATENT DOCUMENTS

| | | |
|---|---|---|
| 6,485,465 B2 | 11/2002 | Moberg et al. |
| 6,500,150 B1 | 12/2002 | Gross et al. |
| 6,503,231 B1 | 1/2003 | Prausnitz et al. |
| 6,511,336 B1 | 1/2003 | Turek et al. |
| 6,517,517 B1 | 2/2003 | Farrugia et al. |
| D471,274 S | 3/2003 | Diaz et al. |
| D471,983 S | 3/2003 | Hippolyte et al. |
| 6,558,351 B1 | 5/2003 | Steil et al. |
| 6,565,541 B2 | 5/2003 | Sharp |
| 6,589,229 B1 | 7/2003 | Connelly et al. |
| 6,595,956 B1 | 7/2003 | Gross et al. |
| 6,595,960 B2 | 7/2003 | West et al. |
| 6,645,181 B1 | 11/2003 | Lavi et al. |
| 6,652,482 B2 | 11/2003 | Hochman |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,689,118 B2 | 2/2004 | Alchas et al. |
| 6,699,218 B2 | 3/2004 | Flaherty et al. |
| 6,722,916 B2 | 4/2004 | Buccinna et al. |
| 6,743,211 B1 | 6/2004 | Prausnitz et al. |
| 6,749,587 B2 | 6/2004 | Flaherty |
| 6,752,787 B1 | 6/2004 | Causey, III et al. |
| 6,768,425 B2 | 7/2004 | Flaherty et al. |
| 6,786,890 B2 | 9/2004 | Preuthun et al. |
| 6,800,071 B1 | 10/2004 | McConnell et al. |
| 6,805,687 B2 | 10/2004 | Dextradeur et al. |
| 6,824,529 B2 | 11/2004 | Gross et al. |
| 6,843,782 B1 | 1/2005 | Gross et al. |
| 6,854,620 B2 | 2/2005 | Ramey |
| 6,905,298 B1 * | 6/2005 | Haring .................. F16B 5/025 411/178 |
| 6,908,452 B2 | 6/2005 | Diaz et al. |
| 6,960,192 B1 | 11/2005 | Flaherty et al. |
| 6,997,727 B1 | 2/2006 | Legrady et al. |
| 7,001,360 B2 | 2/2006 | Veasey et al. |
| 7,034,223 B2 | 4/2006 | Fan et al. |
| 7,048,715 B2 | 5/2006 | Diaz et al. |
| 7,060,054 B2 | 6/2006 | Nissels |
| 7,060,059 B2 | 6/2006 | Keith et al. |
| 7,066,909 B1 | 6/2006 | Peter et al. |
| 7,097,637 B2 | 8/2006 | Triplett et al. |
| 7,128,727 B2 | 10/2006 | Flaherty et al. |
| 7,144,384 B2 | 12/2006 | Gorman et al. |
| D544,092 S | 6/2007 | Lewis |
| 7,225,694 B2 | 6/2007 | Said |
| 7,247,149 B2 | 7/2007 | Beyerlein |
| 7,250,037 B2 | 7/2007 | Shermer et al. |
| 7,267,669 B2 | 9/2007 | Staunton et al. |
| 7,291,132 B2 | 11/2007 | DeRuntz et al. |
| 7,291,159 B2 | 11/2007 | Schmelzeisen-Redeker et al. |
| 7,303,549 B2 | 12/2007 | Flaherty et al. |
| 7,344,385 B2 | 3/2008 | Chen |
| 7,364,570 B2 | 4/2008 | Gerondale et al. |
| 7,390,314 B2 | 6/2008 | Stutz, Jr. et al. |
| 7,407,493 B2 | 8/2008 | Cane' |
| D578,210 S | 10/2008 | Muta et al. |
| 7,455,663 B2 | 11/2008 | Bikovsky |
| 7,465,290 B2 | 12/2008 | Reilly |
| 7,488,181 B2 | 2/2009 | van Haaster |
| 7,497,842 B2 | 3/2009 | Diaz et al. |
| 7,501,587 B2 | 3/2009 | English |
| 7,503,786 B2 | 3/2009 | Kato et al. |
| 7,530,964 B2 | 5/2009 | Lavi et al. |
| 7,540,858 B2 | 6/2009 | DiBiasi |
| 7,547,281 B2 | 6/2009 | Hayes et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| D604,835 S | 11/2009 | Conley |
| 7,628,770 B2 | 12/2009 | Ethelfeld |
| 7,628,772 B2 | 12/2009 | McConnell et al. |
| 7,628,782 B2 | 12/2009 | Adair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,660,627 B2 | 2/2010 | McNichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,913 B2 | 5/2010 | Novak et al. |
| 7,722,574 B2 | 5/2010 | Toman et al. |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,801,599 B2 | 9/2010 | Young et al. |
| 7,806,868 B2 | 10/2010 | De Polo et al. |
| 7,828,528 B2 | 11/2010 | Estes et al. |
| 7,837,659 B2 | 11/2010 | Bush, Jr. et al. |
| 7,846,132 B2 | 12/2010 | Gravesen et al. |
| 7,854,723 B2 | 12/2010 | Hwang et al. |
| 7,857,131 B2 | 12/2010 | Vedrine |
| 7,879,025 B2 | 2/2011 | Jacobson et al. |
| 7,918,825 B2 | 4/2011 | O'Connor et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,105,293 B2 | 1/2012 | Pickhard |
| 8,114,046 B2 | 2/2012 | Covino et al. |
| 8,114,064 B2 | 2/2012 | Alferness et al. |
| 8,114,066 B2 | 2/2012 | Naef et al. |
| D657,462 S | 4/2012 | Siroky |
| 8,147,446 B2 | 4/2012 | Yodfat et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinanen et al. |
| 8,157,693 B2 | 4/2012 | Waksmundzki |
| 8,157,769 B2 | 4/2012 | Cabiri |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |

(56) References Cited

U.S. PATENT DOCUMENTS

| | | |
|---|---|---|
| 8,172,804 B2 | 5/2012 | Bikovsky |
| 8,177,749 B2 | 5/2012 | Slate et al. |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,267,921 B2 | 9/2012 | Yodfat et al. |
| 8,287,520 B2 | 10/2012 | Drew et al. |
| 8,292,647 B1 | 10/2012 | McGrath et al. |
| 8,308,679 B2 | 11/2012 | Hanson et al. |
| 8,323,250 B2 | 12/2012 | Chong et al. |
| 8,372,039 B2 | 2/2013 | Mernoe et al. |
| 8,373,421 B2 | 2/2013 | Lindegger et al. |
| 8,409,142 B2 | 4/2013 | Causey et al. |
| 8,414,557 B2 | 4/2013 | Istoc et al. |
| 8,425,468 B2 | 4/2013 | Weston |
| 8,430,847 B2 | 4/2013 | Mernoe et al. |
| 8,465,455 B2 | 6/2013 | Cabiri |
| 8,469,942 B2 | 6/2013 | Kow et al. |
| 8,474,332 B2 | 7/2013 | Bente, IV et al. |
| 8,475,408 B2 | 7/2013 | Mernoe et al. |
| 8,479,595 B2 | 7/2013 | Vazquez et al. |
| 8,495,918 B2 | 7/2013 | Bazargan et al. |
| 8,496,862 B2 | 7/2013 | Zelkovich et al. |
| 8,512,287 B2 | 8/2013 | Cindrich et al. |
| 8,512,295 B2 | 8/2013 | Evans et al. |
| 8,517,987 B2 | 8/2013 | Istoc et al. |
| 8,523,803 B1 | 9/2013 | Favreau |
| 8,556,856 B2 | 10/2013 | Bazargan et al. |
| 8,562,364 B2 | 10/2013 | Lin et al. |
| 8,574,216 B2 | 11/2013 | Istoc et al. |
| 8,603,026 B2 | 12/2013 | Favreau |
| 8,603,027 B2 | 12/2013 | Favreau |
| 8,628,510 B2 | 1/2014 | Bazargan et al. |
| 8,674,288 B2 | 3/2014 | Hanson et al. |
| 8,679,060 B2 | 3/2014 | Mernoe et al. |
| 8,690,855 B2 | 4/2014 | Alderete, Jr. et al. |
| 8,708,961 B2 | 4/2014 | Field et al. |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |
| 8,814,379 B2 | 8/2014 | Griffiths et al. |
| 8,920,374 B2 | 12/2014 | Bokelman et al. |
| 8,979,802 B2 | 3/2015 | Woehr |
| 9,061,104 B2 | 6/2015 | Daniel |
| 9,061,110 B2 | 6/2015 | Avery et al. |
| 9,089,475 B2 | 7/2015 | Fangrow |
| 9,089,641 B2 | 7/2015 | Kavazov |
| 2001/0018937 A1 | 9/2001 | Nemoto |
| 2001/0025168 A1 | 9/2001 | Gross et al. |
| 2001/0034502 A1 | 10/2001 | Moberg et al. |
| 2001/0041869 A1 | 11/2001 | Causey, III et al. |
| 2002/0010423 A1 | 1/2002 | Gross et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0065488 A1 | 5/2002 | Suzuki et al. |
| 2002/0107487 A1 | 8/2002 | Preuthun |
| 2002/0123740 A1 | 9/2002 | Flaherty et al. |
| 2002/0151855 A1 | 10/2002 | Douglas et al. |
| 2002/0161332 A1 | 10/2002 | Ramey |
| 2002/0169215 A1 | 11/2002 | Meng |
| 2003/0009133 A1 | 1/2003 | Ramey |
| 2003/0014018 A1 | 1/2003 | Giambattista et al. |
| 2003/0125671 A1 | 7/2003 | Aramata et al. |
| 2003/0135159 A1 | 7/2003 | Daily et al. |
| 2003/0160683 A1 | 8/2003 | Blomquist |
| 2003/0171717 A1 | 9/2003 | Farrugia et al. |
| 2004/0010207 A1 | 1/2004 | Flaherty et al. |
| 2004/0049160 A1 | 3/2004 | Hsieh et al. |
| 2004/0049161 A1 | 3/2004 | Shearn |
| 2004/0082911 A1 | 4/2004 | Tiu et al. |
| 2004/0092873 A1* | 5/2004 | Moberg .............. A61M 5/1456 604/131 |
| 2004/0116866 A1 | 6/2004 | Gorman et al. |
| 2004/0127857 A1 | 7/2004 | Shemesh et al. |
| 2004/0158172 A1 | 8/2004 | Hancock |
| 2004/0186419 A1 | 9/2004 | Cho |
| 2004/0186441 A1 | 9/2004 | Graf et al. |
| 2004/0210196 A1 | 10/2004 | Bush, Jr. et al. |
| 2004/0260233 A1 | 12/2004 | Garibotto et al. |
| 2005/0033234 A1 | 2/2005 | Sadowski et al. |
| 2005/0038391 A1 | 2/2005 | Wittland et al. |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0124940 A1 | 6/2005 | Martin et al. |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0203461 A1 | 9/2005 | Flaherty et al. |
| 2005/0238507 A1 | 10/2005 | Dilanni et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0095014 A1 | 5/2006 | Ethelfeld |
| 2006/0122577 A1 | 6/2006 | Poulsen et al. |
| 2006/0173406 A1 | 8/2006 | Hayes et al. |
| 2006/0173439 A1 | 8/2006 | Thorne et al. |
| 2006/0195029 A1 | 8/2006 | Shults et al. |
| 2006/0211982 A1 | 9/2006 | Prestrelski et al. |
| 2006/0229569 A1 | 10/2006 | Lavi et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0049865 A1 | 3/2007 | Radmer et al. |
| 2007/0073228 A1 | 3/2007 | Mernoe et al. |
| 2007/0118405 A1 | 5/2007 | Campbell et al. |
| 2007/0167912 A1 | 7/2007 | Causey et al. |
| 2007/0185449 A1 | 8/2007 | Mernoe |
| 2007/0197954 A1 | 8/2007 | Keenan |
| 2007/0197968 A1 | 8/2007 | Pongpairochana et al. |
| 2007/0203454 A1 | 8/2007 | Shermer et al. |
| 2007/0233038 A1 | 10/2007 | Pruitt et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097381 A1 | 4/2008 | Moberg et al. |
| 2008/0108951 A1 | 5/2008 | Jerde et al. |
| 2008/0140006 A1 | 6/2008 | Eskuri et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0208138 A1 | 8/2008 | Lim et al. |
| 2008/0215006 A1 | 9/2008 | Thorkild |
| 2008/0215013 A1 | 9/2008 | Felix-Faure |

(56) References Cited

U.S. PATENT DOCUMENTS

| | | |
|---|---|---|
| 2008/0215015 A1 | 9/2008 | Cindrich et al. |
| 2008/0243087 A1 | 10/2008 | Enggaard et al. |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319416 A1 | 12/2008 | Yodfat et al. |
| 2009/0012478 A1 | 1/2009 | Weston |
| 2009/0041805 A1 | 2/2009 | Walker |
| 2009/0048347 A1 | 2/2009 | Cohen et al. |
| 2009/0054750 A1 | 2/2009 | Jennewine |
| 2009/0069784 A1 | 3/2009 | Estes et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093792 A1 | 4/2009 | Gross et al. |
| 2009/0093793 A1 | 4/2009 | Gross et al. |
| 2009/0105650 A1 | 4/2009 | Wiegel et al. |
| 2009/0124977 A1 | 5/2009 | Jensen |
| 2009/0143730 A1 | 6/2009 | De Polo et al. |
| 2009/0143735 A1 | 6/2009 | De Polo et al. |
| 2009/0149830 A1 | 6/2009 | Spector |
| 2009/0182277 A1 | 7/2009 | Carter |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0281585 A1 | 11/2009 | Katzman et al. |
| 2009/0299288 A1 | 12/2009 | Sie et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326509 A1 | 12/2009 | Muse et al. |
| 2010/0030156 A1 | 2/2010 | Beebe et al. |
| 2010/0030198 A1 | 2/2010 | Beebe et al. |
| 2010/0049128 A1 | 2/2010 | McKenzie et al. |
| 2010/0049144 A1 | 2/2010 | McConnell et al. |
| 2010/0057057 A1 | 3/2010 | Hayter et al. |
| 2010/0076382 A1 | 3/2010 | Weston |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0234767 A1 | 9/2010 | Sarstedt |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0125056 A1 | 5/2011 | Merchant |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |
| 2011/0178472 A1 | 7/2011 | Cabiri |
| 2011/0201998 A1 | 8/2011 | Pongpairochana et al. |
| 2011/0224616 A1 | 9/2011 | Slate et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041414 A1 | 2/2012 | Estes et al. |
| 2012/0071828 A1 | 3/2012 | Tojo et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0172817 A1* | 7/2012 | Bruggemann .... A61M 5/14566 604/218 |
| 2012/0226234 A1 | 9/2012 | Bazargan et al. |
| 2012/0259282 A1 | 10/2012 | Alderete, Jr. et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0133438 A1 | 5/2013 | Kow et al. |
| 2013/0190693 A1 | 7/2013 | Ekman et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0253419 A1 | 9/2013 | Favreau |
| 2013/0253420 A1 | 9/2013 | Favreau |
| 2013/0253421 A1 | 9/2013 | Favreau |
| 2013/0296799 A1 | 11/2013 | Degtiar et al. |
| 2013/0304021 A1 | 11/2013 | Cabiri et al. |
| 2013/0323699 A1 | 12/2013 | Edwards et al. |
| 2013/0331791 A1 | 12/2013 | Gross et al. |
| 2013/0338584 A1 | 12/2013 | Mounce et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0128807 A1 | 5/2014 | Moberg et al. |
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete, Jr. et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0213975 A1 | 7/2014 | Clemente et al. |
| 2014/0236087 A1 | 8/2014 | Alderete, Jr. et al. |
| 2014/0261758 A1 | 9/2014 | Wlodarczyk et al. |

(56) References Cited

U.S. PATENT DOCUMENTS

FOREIGN PATENT DOCUMENTS

| | | |
|---|---|---|
| CN | 101090749 A | 12/2007 |
| CN | 101227943 A | 7/2008 |
| CN | 101448536 A | 6/2009 |
| CN | 101522235 A | 9/2009 |
| CN | 101541362 A | 9/2009 |
| CN | 201692438 U | 1/2011 |
| CN | 201941304 U | 8/2011 |
| CN | 102186733 A | 9/2011 |
| CN | 102378638 A | 3/2012 |
| DE | 1064693 B | 9/1959 |
| DE | 19717107 A1 | 11/1998 |
| EP | 0017412 A1 | 10/1980 |
| EP | 0222656 A1 | 5/1987 |
| EP | 0401179 A1 | 12/1990 |
| EP | 1530979 A1 | 5/2005 |
| EP | 1666080 A1 | 6/2006 |
| EP | 2060606 A1 | 5/2009 |
| EP | 2498589 A1 | 9/2012 |
| JP | H07-194701 A | 8/1995 |
| JP | H09-505758 A | 6/1997 |
| JP | 2001-512992 A | 8/2001 |
| JP | 2002-505601 A | 2/2002 |
| JP | 2002-507459 A | 3/2002 |
| JP | 2002-528676 A | 9/2002 |
| JP | 2003-501157 A | 1/2003 |
| JP | 2003-527138 A | 9/2003 |
| JP | 2003-534061 A | 11/2003 |
| JP | 2004-501721 A | 1/2004 |
| JP | 2004-512100 A | 4/2004 |
| JP | 2005-523127 A | 8/2005 |
| JP | 2005-270629 A | 10/2005 |
| JP | 2007-509661 A | 4/2007 |
| JP | 2008-534131 A | 8/2008 |
| JP | 2008-220961 A | 9/2008 |
| JP | 2009-502273 A | 1/2009 |
| WO | 9009202 A1 | 8/1990 |
| WO | 9307922 A1 | 4/1993 |
| WO | 9407553 A1 | 4/1994 |
| WO | 9513838 A1 | 5/1995 |
| WO | 9609083 A1 | 3/1996 |
| WO | 9632975 A1 | 10/1996 |
| WO | 9700091 A1 | 1/1997 |
| WO | 9710012 A1 | 3/1997 |
| WO | 9733638 A1 | 9/1997 |
| WO | 9857683 A1 | 12/1998 |
| WO | 9929151 A1 | 6/1999 |
| WO | 9959665 A1 | 11/1999 |
| WO | 0025844 A1 | 5/2000 |
| WO | 0187384 A1 | 11/2001 |
| WO | 0189607 A2 | 11/2001 |
| WO | 0189613 A1 | 11/2001 |
| WO | 0202165 A2 | 1/2002 |
| WO | 0234315 A1 | 5/2002 |
| WO | 0272182 A1 | 9/2002 |
| WO | 03090833 A1 | 11/2003 |
| WO | 2004032990 A2 | 4/2004 |
| WO | 2004105841 A1 | 12/2004 |
| WO | 2005018703 A2 | 3/2005 |
| WO | 2005037350 A2 | 4/2005 |
| WO | 2005072795 A2 | 8/2005 |
| WO | 2006037434 A1 | 4/2006 |
| WO | 2006069380 A1 | 6/2006 |
| WO | 2006102676 A1 | 9/2006 |
| WO | 2006104806 A2 | 10/2006 |
| WO | 2007017052 A1 | 2/2007 |
| WO | 2007051563 A1 | 5/2007 |
| WO | 2007056504 A1 | 5/2007 |
| WO | 2007073228 A1 | 6/2007 |
| WO | 2008001377 A2 | 1/2008 |
| WO | 2008014908 A1 | 2/2008 |
| WO | 2008057976 A2 | 5/2008 |
| WO | 2008072229 A2 | 6/2008 |
| WO | 2008076459 A1 | 6/2008 |
| WO | 2008078318 A2 | 7/2008 |
| WO | 2009044401 | 4/2009 |
| WO | 2009046989 A2 | 4/2009 |
| WO | 2009125398 A2 | 10/2009 |
| WO | 2009144085 A2 | 12/2009 |
| WO | 2010078227 A1 | 7/2010 |
| WO | 2010078242 A1 | 7/2010 |
| WO | 2010089313 A1 | 8/2010 |
| WO | 2011075105 A1 | 6/2011 |
| WO | 2011090955 A1 | 7/2011 |
| WO | 2011090956 A2 | 7/2011 |
| WO | 2011156373 A1 | 12/2011 |
| WO | 2012032411 A2 | 3/2012 |
| WO | 2012040528 A1 | 3/2012 |
| WO | 2012160157 A1 | 11/2012 |
| WO | 2014179774 A1 | 11/2014 |

OTHER PUBLICATIONS

Office Action issued Nov. 5, 2013 in JP Application No. 2010-527595.
Office Action issued Sep. 29, 2013 in CN Application No. 201080040968.7.
Office Action issued Nov. 4, 2013 in EP Application No. 11 709 234.6.
Office Action issued Nov. 5, 2014 in U.S. Appl. No. 13/643,470 by Alon.
U.S. Appl. No. 14/553,399 by Cabiri, filed Nov. 25, 2014.
Office Action issued Nov. 2, 2014 in CN Application No. 201180006571.0.
Office Action issued Nov. 21, 2014 in U.S. Appl. No. 13/472,112 by Cabiri.
Office Action issued Nov. 21, 2014 in U.S. Appl. No. 13/429,840 by Cabiri.
Int'l Preliminary Report on Patentability issued Nov. 27, 2014 in Int'l Application No. PCT/US2013/039465.
Office Action issued Jul. 31, 2015 in U.S. Appl. No. 13/521,181 by Cabiri.
Office Action issued Aug. 13, 2015 in U.S. Appl. No. 14/553,399 by Cabiri.
Int'l Preliminary Report on Patentability issued Jul. 16, 2015 in Int'l Application No. PCT/US2013/078040.
Notice of Allowance issued Aug. 24, 2015 in U.S. Appl. No. 29/479,307 by Norton.
Extended European Search Report issued Aug. 7, 2014 in EP Application No. 1417477.4.
Office Action issued Aug. 6, 2014 in EP Application No. 11 707 942.6.
Office Action issued Sep. 2, 2014 in JP Application No. 2012-550069.
Office Action issued Sep. 2, 2014 in JP Application No. 2012-550068.
Office Action issued Aug. 26, 2014 in CN Application No. 201180006567.4.
Int'l Preliminary Report on Patentability issued Oct. 9, 2014 in Int'l Application No. PCT/US2013/033118.
Office Action issued Oct. 9, 2014 in U.S. Appl. No. 13/873,335.
Extended European Search Report issued Mar. 8, 2016 in EP Application No. 14166592.7.
U.S. Appl. No. 14/593,051 by Gross, filed Jan. 9, 2015.
U.S. Appl. No. 14/683,193 by Cabiri, filed Apr. 10, 2015.
Office Action issued Feb. 20, 2015 in U.S. Appl. No. 13/521,181 by Cabiri.
Office Action issued Feb. 24, 2015 in U.S. Appl. No. 14/258,661 by Cabiri.
U.S. Appl. No. 14/638,525 by Filman, filed Mar. 4, 2015.
Extended European Search Report issued Feb. 23, 2015 in EP Application No. 14166596.8.
Office Action issued Mar. 10, 2015 in U.S. Appl. No. 13/643,470 by Alon.
Office Action issued Mar. 10, 2015 in U.S. Appl. No. 12/244,666 by Gross.

(56) References Cited

OTHER PUBLICATIONS

Extended European Search Report issued Feb. 23, 2015 in EP Application No. 14166591.9.
Office Action issued Mar. 10, 2015 in CN Application No. 201180006567.4.
Office Action issued Mar. 31, 2015 in JP Application No. 2012-550068.
Daikyo Crystal Zenith® polymer, Manufactured by Daikyo Seiko, Ltd.
Copaxone® , Manufactured by Teva Pharmaceutical Industries Ltd.
Int'l Search Report issued May 13, 2009 in Int'l Application No. PCT/IL2008/001312.
Int'l Preliminary Report on Patentability issued Apr. 7, 2010 in Int'l Application No. PCT/IL2008/001312; Written Opinion.
Int'l Search Report issued Apr. 26, 2010 in Int'l Application No. PCT/US2009/069552.
Office Action issued Apr. 5, 2010 in U.S. Appl. No. 12/244,666.
Office Action issued Sep. 21, 2010 in U.S. Appl. No. 12/244,666.
Office Action issued Apr. 5, 2010 in U.S. Appl. No. 12/244,688.
Office Action issued Sep. 2, 2010 in U.S. Appl. No. 12/244,688.
Office Action issued Sep. 30, 2010 in U.S. Appl. No. 12/689,250.
Int'l Search Report issued Jan. 12, 2011 in Int'l Application No. PCT/US2010/048556; Written Opinion.
International Preliminary Report on Patentability issued on Jul. 5, 2011 in International Application No. PCT/US2009/069552; Written Opinion.
Office Action issued Jul. 13, 2011 in U.S. Appl. No. 12/559,563.
Int'l Preliminary Report on Patentability issued Sep. 1, 2011 in Int'l Application No. PCT/US2010/048556.
Office Action issued Sep. 6, 2011 in U.S. Appl. No. 12/345,818.
Office Action issued Feb. 21, 2012 in U.S. Appl. No. 12/689,249.
Int'l Search Report issued Jun. 17, 2011 in Int'l Application No. PCT/US2011/021604.
Int'l Search Report issued Oct. 12, 2011 in Int'l Application No. PCT/US2011/021605.
Office Action issued Oct. 28, 2011 in U.S. Appl. No. 12/615,828.
Int'l Search Report issued Sep. 22, 2011 in Int'l Application No. PCT/IL11/00368; Written Opinion.
U.S. Appl. No. 13/521,181 by Cabiri, filed Jul. 9, 2012.
U.S. Appl. No. 13/521,167 by Cabiri, filed Jul. 9, 2012.
Office Action issued May 16, 2012 in U.S. Appl. No. 12/615,828.
Office Action issued Jul. 2, 2012 in U.S. Appl. No. 13/272,555.
Office Action issued May 3, 2012 in CN Application No. 200880117084.X.
U.S. Appl. No. 13/472,112 by Cabiri, filed May 15, 2012.
U.S. Appl. No. 13/429,840 by Cabiri, filed Mar. 26, 2012.
Int'l Preliminary Report on Patentability issued Aug. 2, 2012 in Int'l Application No. PCT/US2011/021604.
U.S. Appl. No. 13/643,470 by Alon, filed Oct. 25, 2012.
U.S. Appl. No. 13/733,516 by Cabiri, filed Jan. 3, 2013.
Office Action issued Jan. 8, 2013 in JP Application No. 2010-527595.
Int'l Preliminary Report on Patentability issued Feb. 7, 2013 in Int'l Application No. PCT/US2011/021604.
Int'l Preliminary Report on Patentability issued Feb. 7, 2013 in Int'l Application No. PCT/US2011/021605.
English translation of an Office Action issued Jan. 30, 2013 in CN Application No. 200880117084.X.
U.S. Appl. No. 13/873,335 by Filman, filed Apr. 30, 2013.
U.S. Appl. No. 13/892,905 by Cabiri, filed May 13, 2013.
U.S. Appl. No. 13/874,121 by Degtiar, filed Apr. 30, 2013.
U.S. Appl. No. 13/874,085 by Cabiri, filed Apr. 30, 2013.
Int'l Preliminary Report on Patentability issued May 14, 2015 in Int'l Application No. PCT/US2013/065211.
Office Action issued May 7, 2015 in JP Application No. 2012-550069.
Office Action issued May 13, 2015 in CN Application No. 201380025566.3.
U.S. Appl. No. 14/715,791 by Cabiri, filed May 19, 2015.
U.S. Appl. No. 14/725,009 by Bar-El, filed May 29, 2015.
Office Action issued May 1, 2015 in U.S. Appl. No. 14/638,525 by Filman.
Office Action issued Jun. 4, 2015 in U.S. Appl. No. 13/667,739 by Cabiri.
Office Action issued Jun. 3, 2014 in JP Application No. 2010-527595.
Office Action issued Jul. 7, 2014 in U.S. Appl. No. 12/244,666 by Gross.
Int'l Search Report and Written Opinion issued Jul. 31, 2014 in Int'l Application No. PCT/US2014/033598.
Int'l Search Report and Written Opinion issued Jul. 26, 2013 in Int'l Application No. PCT/US2012/039465.
Int'l Search Report and Written Opinion issued Aug. 5, 2013 in Int'l Application No. PCT/US2013/033118.
U.S. Appl. No. 13/964,651 by Gross, filed Aug. 12, 2013.
Office Action issued Aug. 15, 2013 in CN Application No. 200880117084.X.
Office Action issued Dec. 17, 2013 in JP Application No. 2012-529808.
Office Action issued Dec. 10, 2013 in CN Application No. 201180006567.4.
Office Action issued Jan. 8, 2014 in U.S. Appl. No. 13/521,167 by Cabiri.
U.S. Appl. No. 29/479,307 by Norton, filed Jan. 14, 2014.
Partial European Search Report issued Nov. 24, 2015 in EP Application No. 141665921.
Office Action issued Dec. 1, 2015 in CN Application No. 201410289204.1.
U.S. Appl. No. 14/193,692 by Gross, filed Feb. 28, 2014.
Office Action issued Feb. 4, 2014 in EP Application No. 11 707 942.6.
English translation of an Office Action issued Mar. 5, 2014 in CN Application No. 200880117084.X.
Int'l Search Report and Written Opinion issued Apr. 3, 2014 in Int'l Application No. PCT/US2013/078040.
Extended European Search Report issued Mar. 27, 2014 in EP Application No. 14154717.4.
Office Action issued Feb. 28, 2014 in CN Application No. 201180006571.0.
U.S. Appl. No. 14/258,661 by Cabiri, filed Apr. 22, 2014.
Int'l Search Report and Written Opinion issued Jan. 7, 2014 in Int'l Application No. PCT/US2013/065211.
Office Action issued May 23, 2014 in U.S. Appl. No. 13/472,112 by Cabiri.
Office Action issued Sep. 9, 2015 in U.S. Appl. No. 13/643,470 by Alon.
U.S. Appl. No. 14/850,450 by Gross, filed Sep. 10, 2015.
U.S. Appl. No. 14/861,478 by Cabiri, filed Sep. 22, 2015.
U.S. Appl. No. 14/880,673 by Cabiri, filed Oct. 12, 2015.
Office Action issued Sep. 30, 2015 in U.S. Appl. No. 13/667,739 by Cabiri.
Office Action issued Sep. 18, 2015 in U.S. Appl. No. 13/874,085 by Cabiri.
Office Action issued Jun. 10, 2016 in U.S. Appl. No. 13/964,651 by Gross.
Office Action issued May 31, 2016 in U.S. Appl. No. 14/593,051 by Gross.
Office Action issued Apr. 22, 2016 in CN Application No. 2014102892041.
Office Action issued May 5, 2015 in CN Application No. 201180006571.0.
Office Action issued Jun. 2, 2016 in CN Application No. 2014101783189.
Office Action issued Nov. 10, 2016 in U.S. Appl. No. 13/874,121, by Degtiar.
Office Action issued Oct. 5, 2016 in U.S. Appl. No. 13/964,651, by Gross.
Dffice Action issued Dec. 9, 2016 in U.S. Appl. No. 14/593,051, by Gross.
Search Report issued Oct. 14, 2016 in CN Application No. 2014101783742.
Office Action issued Oct. 28, 2016 in CN Application No. 2014101783742.

(56) References Cited

OTHER PUBLICATIONS

Office Action issued Jan. 10, 2017 in U.S. Appl. No. 14/193,692, by Gross.

* cited by examiner

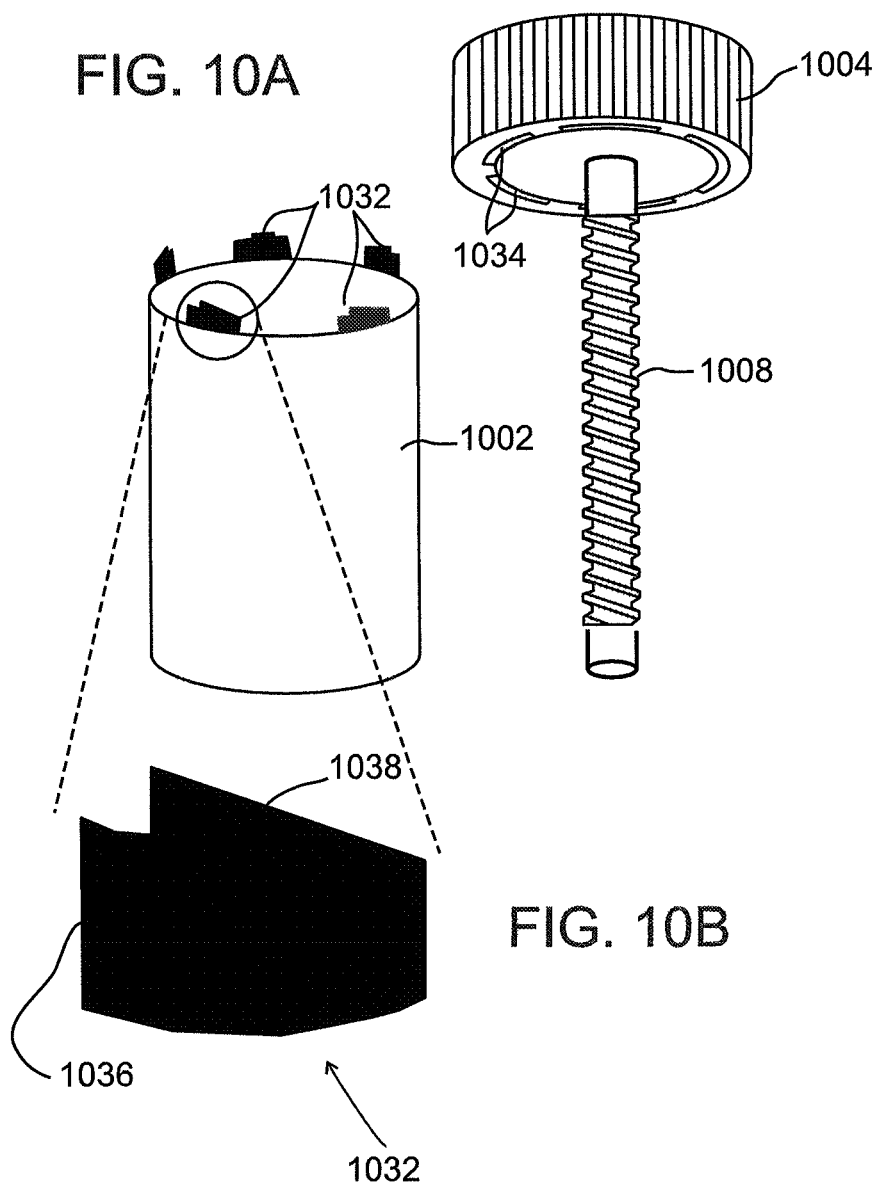

APPARATUSES FOR SECURING COMPONENTS OF A DRUG DELIVERY SYSTEM DURING TRANSPORT AND METHODS OF USING SAME

CROSS-REFERENCE TO RELATED APPLICATIONS

This application is a Continuation-in-Part of U.S. patent application Ser. No. 12/244,666, filed on Oct. 2, 2008, now U.S. Pat. No. 9,173,997, issued Nov. 3, 2015, which claims priority to U.S. Provisional patent application No. 60/997,459, filed Oct. 2, 2007. This application is also a Continuation-in-Part of U.S. application Ser. No. 13/521,181, filed on Jul. 9, 2012, now U.S. Pat. No. 9,259,532, issued Feb. 16, 2016, which is a 371 of International Patent Application No. PCT/US2011/21605, filed on Jan. 19, 2011, which is a Continuation of U.S. patent application Ser. No. 12/689,250, filed on Jan. 19, 2010, now U.S. Pat. No. 7,967,795, issued Jun. 28, 2011, the disclosures of all of which are incorporated by reference herein.

This application is also related to U.S. patent application Ser. No. 13/874,085, filed on Apr. 30, 2013, now U.S. Pat. No. 9,345,836, issued May 24, 2016, the disclosure of which is incorporated herein by reference.

BACKGROUND OF THE INVENTION

The present invention, in some embodiments thereof, relates to drug delivery systems and, more particularly, but not exclusively, to apparatuses and methods for securing components of a drug delivery system during transport.

International Patent Application Publication No. WO 2011/090956, which is incorporated herein by reference, discloses a cartridge interface assembly characterized by a driving plunger including an outer shaft and a driver including an inner shaft movable telescopically with respect to the outer shaft, wherein rotation of the driver causes the driving plunger to advance in a direction away from the driver, and wherein the cartridge interface assembly is inserted in a cartridge in which a plunger is slidingly disposed, and rotation of the driver causes the driving plunger to advance distally in the cartridge until abutting against the plunger. To solve the problem of possible opening of telescoping shafts during transportation and handling before assembly, with the result that the position which is the desirable position for assembly with the cartridge plunger, is not maintained, a locking assembly is provided. The driver is formed with a recess, bounded by a wall. The proximal end of the body of the cartridge interface assembly is formed with a locking tooth. In the assembly configuration the locking tooth is received in the recess. The locking tooth is formed with a slanted wall. The slanted walls can glide over the edge of the recess. Thus, the locking assembly enables easy assembly of the telescoping shaft assembly with the plunger, and maintains the desired position of the driver. The locking assembly prevents the telescoping shaft assembly from opening during transportation and handling, and ensures a small opening torque during operation.

BRIEF SUMMARY OF THE INVENTION

An aspect of some embodiments of the invention relates to providing resistance to linear motion of an assembly of a drug delivery system to secure the assembly during transport. In some embodiments of the invention, the drug delivery system is a patch injector. In some embodiments of the invention, the assembly is telescoping. In some embodiments of the invention, the assembly is threaded or at least two components of the assembly are operatively connected by threading.

In an exemplary embodiment of the invention, resistance is provided to the telescoping assembly by configuring at least a portion of the telescoping with an annular ring and a corresponding counterpart lip, wherein the annular ring (or a portion of a ring) is forced against the lip to create resistance to motion of the telescoping assembly.

In some embodiments of the invention, the torque required to overcome the resistance between the annular ring and the lip is approximately equal to or less than the torque required to stall the driving motor, but is still greater than the extending threes expected to be encountered by the telescoping assembly during transport. In some embodiments of the invention, the motor is selected based on its ability to supply sufficient torque to overcome the resistance. In some embodiments of the invention, circuitry is provided which allows for the torque applied by the motor to be varied such that a level of torque that is selected is sufficient to overcome the resistance.

In some embodiments of the invention, the annular ring is provided to a pushing nut screw of the telescoping assembly, and the corresponding lip is provided to a cartridge gear of the telescoping assembly. In some embodiments of the invention, the annular ring extends around the outer circumference of the pushing nut screw. In some embodiments of the invention, the annular ring extends only partially around the outer circumference of the pushing nut screw. In an exemplary embodiment of the invention, the lip is configured on the cartridge gear to correspond to the location of the annular ring on the pushing nut screw.

In an embodiment of the invention, the annular ring and/or the lip are made of the same material as the pushing nut screw and/or the cartridge gear, respectively. Optionally, the annular ring and/or lip are constructed of a different material than the pushing nut screw and/or cartridge gear, respectively.

In an embodiment of the invention, the annular ring and lip are located in the telescoping assembly such that they come into contact prior to the telescoping assembly encountering resistance from injecting the fluid of the drug delivery system in which the telescoping assembly is installed.

In some embodiments of the invention, resistance is provided to the telescoping assembly by increasing the friction of at least one of the first few threads, turns or parts of threads/turns of an internal screw of the telescoping assembly. In some embodiments of the invention, at least one of the first few threads is tighter and/or less deep. In some embodiments of the invention, the shape of the internal screw is not perfectly round. Additionally, alternatively and/or optionally, at least one of the first few threads is coated with an adhesive and/or abrasive material or is surface finished, like by, sandblasting, which increases friction An aspect of some embodiments of the invention relates to a method for using a telescoping assembly including securing it for transport. In an embodiment of the invention, the telescoping assembly is provided (manufactured) with resistance to turning, thereby securing it for transport. Optionally, the telescoping assembly is closed for transport after manufacturing. Optionally, the telescoping assembly is manufactured in the closed, transport configuration. The closed telescoping assembly is placed into a drug delivery system, for example a patch injector. As the drug delivery system is activated, resistance is overcome within the first few twists of an internal screw of the telescoping assembly.

In some embodiments of the invention, resistance is provided by pushing an annular ring against a lip and using the friction between them and/or the force required to deform a portion of an assembly component. In some embodiments of the invention, resistance is provided by increasing the friction against twisting of at least one of the first few threads of a screw of the telescoping assembly. Optionally, the resistance is provided during manufacturing.

In some embodiments, after continued torque applied by a motor of the drug delivery system overcomes this initial and/or temporary resistance, further extension of the telescoping assembly discharges the fluid in a cartridge of the drug delivery system into a patient.

There is provided in accordance with an exemplary embodiment of the invention, an assembly of a drug delivery system, comprising: a first component; a second component which is configured to move linearly with respect to the first component; and, a resistance element configured to resist movement during transport of the first component with respect to the second component at a predetermined relative location between the first and second components but which is adapted to be overcome during nominal operation of the drug delivery system.

In an embodiment of the invention, the first component and the second component are threaded together and linear movement is achieved by rotation of at least one of the first component and the second component.

In an embodiment of the invention, the predetermined relative location is before the linear movement of the second component with respect to the first component effectuates pumping in the drug delivery system.

In an embodiment of the invention, the second component is a pushing element and the first component is a drive element.

In an embodiment of the invention, the resistance element is an annular ring and a counterpart lip.

In an embodiment of the invention, a pushing element is provided with the annular ring and a drive element is provided with the counterpart lip, which when the ring and the lip are forced together create the resistance to extension of the assembly.

In an embodiment of the invention, the first component is an internal screw.

In an embodiment of the invention, at least one of a first few threads of the internal screw are configured with increased friction in relation to the other threads of the internal screw. Optionally, the at least one of a first few threads of the internal screw is provided with increased friction by making a gap between the at least one thread and the next thread tighter. Optionally, the at least one of a first few threads of the internal screw is provided with increased friction by making the at least one thread less deep than the other threads of the internal screw. Optionally, the at least one of a first few threads of the internal screw is provided with increased friction by altering the shape of the screw to increase friction between threads as it turns. Optionally, the at least one of a first few threads is provided with increased friction by coating the thread with at least one of an abrasive material and an adhesive material. Optionally, the first few threads are located on the internal screw such that turning the internal screw through the first few threads do not activate the pressure exerting component of the telescoping assembly.

In an embodiment of the invention, the torque required to overcome the resistance element is equal or less than the nominal operative torque required to stall a driving motor of the drug delivery system.

In an embodiment of the invention, the required torque to overcome the resistance element is varied from 50-300 gr-cm.

In an embodiment of the invention, the resistance element is overcome by deformation of at least a portion of at least one of the first and second components.

In an embodiment of the invention, the deformation is at least one of elastic and plastic deformation.

In an embodiment of the invention, the resistance element includes a sloped contact surface.

There is provided in accordance with an exemplary embodiment of the invention, a method of using an assembly of a drug delivery system, comprising: providing resistance to linear extension of the assembly when the assembly is in a closed configuration; placing the closed assembly into the drug delivery system; activating the drug delivery system; applying torque to overcome the provided resistance; and, extending the assembly to exert pressure on a fluid in a cartridge of the drug delivery system.

In an embodiment of the invention, the method further comprises closing the assembly prior to the placing.

In an embodiment of the invention, providing resistance comprises abutting an annular ring of a pushing element of the assembly with a lip of a drive element of the telescoping assembly to distribute the resistance over a large area.

In an embodiment of the invention, providing resistance is distributed over a plurality of separate portions of an annular ring.

In an embodiment of the invention, providing resistance comprises heightening the friction against turning for at least one of a first few threads of an internal screw of the assembly. Optionally, heightening the friction comprises at least one of narrowing the gap between threads, making the threads less deep and shaping the internal screw irregularly. Optionally, heightening the friction comprises coating the at least one thread with at least one of an abrasive material and an adhesive material.

There is provided in accordance with an exemplary embodiment of the invention, a method of transporting an assembly of a drug delivery system, comprising: manufacturing the assembly to include at least one resistance element adapted to resist vibrations which cause unintentional extension of the assembly but which is overcome by a required torque during nominal operation of the drug delivery system; configuring the assembly for transport; and, transporting the telescoping assembly.

In an embodiment of the invention, the required torque to overcome the resistance element is at least 50 gr-cm.

In an embodiment of the invention, the required torque to overcome the resistance element is at least 100 gr-cm.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, are not to scale, and are for purposes of illustrative discussion of embodiments of the invention. In this regard, the description taken with the drawings makes apparent to those skilled in the art how embodiments of the invention may be practiced.

In the drawings:

FIGS. 10A-10B are schematic illustrations of an alternate embodiment of an assembly having a resistance element, in accordance with an exemplary embodiment of the invention.

DETAILED DESCRIPTION OF THE INVENTION

Figure 1:
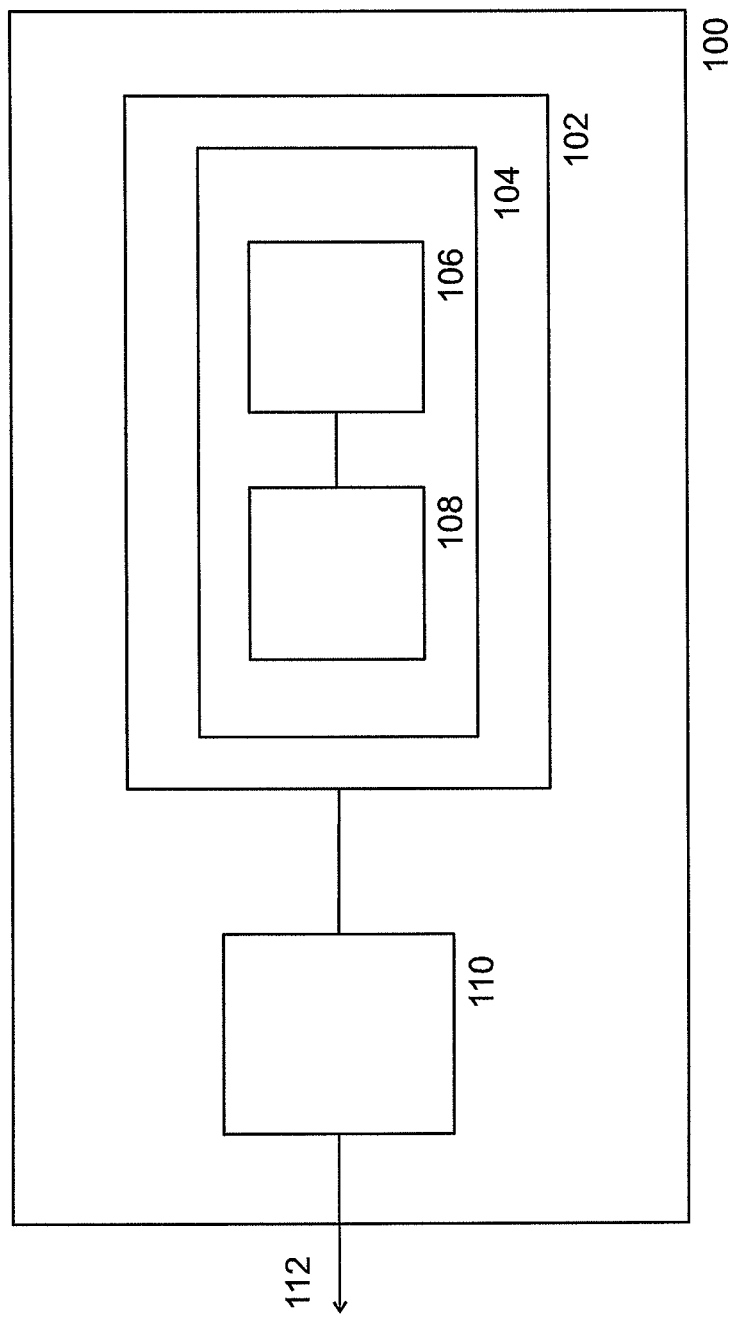
FIG. 1 is a schematic block diagram illustrating a system for preventing unintended extension of an assembly of a drug delivery system, in accordance with an exemplary embodiment of the invention

The present invention, in some embodiments thereof, relates to drug delivery systems and, more particularly, but not exclusively, to apparatuses and methods for securing components of a drug delivery system during transport.

Failure to use a delivery device or system, such as an insulin pen or auto-injector, correctly could result in a life or death emergency, or impact a patient's or caregiver s ability to manage a medical condition effectively. For the pharmaceutical manufacturer, such a failure could result in a massive backlash that may cause loss of market share, costly product recalls or worse.

A primary goal of any drug delivery system is to ensure'that a patient receives a proper dose of a prescribed drug. In years past, if a device failed or was used incorrectly, patient or caregiver error was most often the culprit. While providing detailed instructions is important for any pharmaceutical manufacturer, failure to follow directions is no longer a viable excuse when a patient or caregiver is unable to operate a device or delivery system successfully.

Effective drug therapy and treatment often involves more than simply having an effective molecule. Rather, it is the combination of a safe drug within a suitable container and/or delivery system.

Historically, pharmaceutical manufacturers have focused, and rightly so, on the efficacy and safety of the drug product. However, if the drug is to achieve its therapeutic objective, then its primary container and delivery system must be both compatible with the drug and stable over time, as well as foster adherence from the patient. A drug can only truly have the desired patient benefit if it is taken as prescribed, delivered effectively (often by a patient or caregiver), and maintains performance over time Today's injectable therapies can take many forms. Liquid drugs may use a traditional syringe and vial; a prefilled syringe; or a delivery system such as an auto-injector, pen device or patch injector. Lyophilized drug products (requiring reconstitution with water for injection) may require a kit containing a transfer device, syringe or needle, and containers of the drug and water.

The container format itself also should be considered. Vials may be necessary for initial use, but a syringe or cartridge system may provide the best solution for the patient when the system reaches the market. Once the primary container has been selected, efforts must be made to ensure that it works with the delivery system. Dimensional tolerances and functionality should be tested to ensure proper activation and gliding forces.

Recognizing how the patient or caregiver interacts with the delivery system is essential to ensuring success in the market. Even the most innovative drug can provide the appropriate therapeutic benefit to the patient only if it can be delivered effectively and the patient adheres to the necessary treatment regimen. Patients or caregivers may choose one product over another based on dose frequency, pain associated with dosing, or ease of use or mobility of the delivery system. Simply put, packaging can differentiate a product's market acceptance.

One potential issue associated with patch injectors is movement of the operative parts during transport. For, example, vibrations during transport may cause movements of screws causing a telescoping assembly of the delivery system to extend. As result, when a cartridge containing the unintentionally extended telescoping assembly is inserted by the user, it may be difficult to close the door of the delivery system, for example. Some users may interpret this as a malfunction and elect not use the unit.

Before explaining at least one embodiment of the invention in detail, it is to be understood that the invention is not necessarily limited in its application to the details of construction and the arrangement of the components and/or methods set forth in the following description and/or illustrated in the drawings and/or the exemplary embodiments. The invention is capable of other embodiments or of being practiced or carried out in various ways.

Referring now to the drawings, FIG. 1 is a schematic block diagram illustrating a configuration for preventing unintended linear extension of a telescoping assembly 102 of a drug delivery system 100 during transport, in accordance with an exemplary embodiment of the invention.

In an embodiment of the invention, telescoping assembly 102 is comprised of at least one component 104, including at least a driving element 106 and a pushing element 108. In an embodiment of the invention, the pushing element is operatively attached to a plunger or stopper in a cartridge 110 of the drug delivery system 100, where the plunger provides a fluid-proof seal against the fluid (e.g. pharmaceutical) in the cartridge 110 and which pumps the, fluid out 112 of the cartridge and into the patient when the telescoping assembly 102 extends and activates/instigates the pushing of the pushing element by using the driving element to push/extend the pushing element. In an embodiment of the invention, the telescoping assembly 102 optionally has a plurality of components 104 which functionally act in concert to effectuate extension of the telescoping assembly. For example, telescoping assembly 102 could be constructed of 2, 3, or 4 or more components, such as rods and/or screws and/or those components described herein.

In an embodiment of the invention, at least one component 104 of the telescoping assembly 102 is provided with a resistance element to substantially prevent or entirely prevent unintended linear extension of the telescoping assembly 102. In some embodiments of the invention, unintentional extension of the telescoping assembly 102 includes extension as a result of vibration of the assembly 102 during transport. In an embodiment of the invention, the resistance element provides resistance to the linear extension of one component of the telescoping assembly 102 with respect to at least one other component of the telescoping assembly 102.

In an embodiment of the invention, the drug delivery system 100 is a patch injector system. Patch injectors are among new technologies for enabling self-administration of large molecule and viscous biologics. Patch injector systems that are tailored to the needs of the end user provide an excellent example of the balance between an effective drug containment system and a user-friendly delivery system. For example, with a patch injector system, the patient can take a large volume injection with just one needle stick, where one might need multiple needle sticks with a standard auto-injector, pen, or syringe. In spite of internal system complexity, patch injector systems can be designed for simplicity and patient comfort, while facilitating the delivery of drug products. In some embodiments of the invention, the telescoping assembly 102 is an operative component of a cartridge of a patch injector system, wherein the disposable and/or interchangeable cartridge contains a pre-measured dose of a drug to be administered to a patient using the drug delivery system.

It should be understood that in order to utilize a smaller, more economical motor, the torque required to screw the telescoping assembly 102 in order to linearly extend and retract it is minimized with low friction threading. This low friction threading allows for easier movement using the motor, but it is also what allows for easy unintended extension of the assembly 102 during transport.

Figure 2:
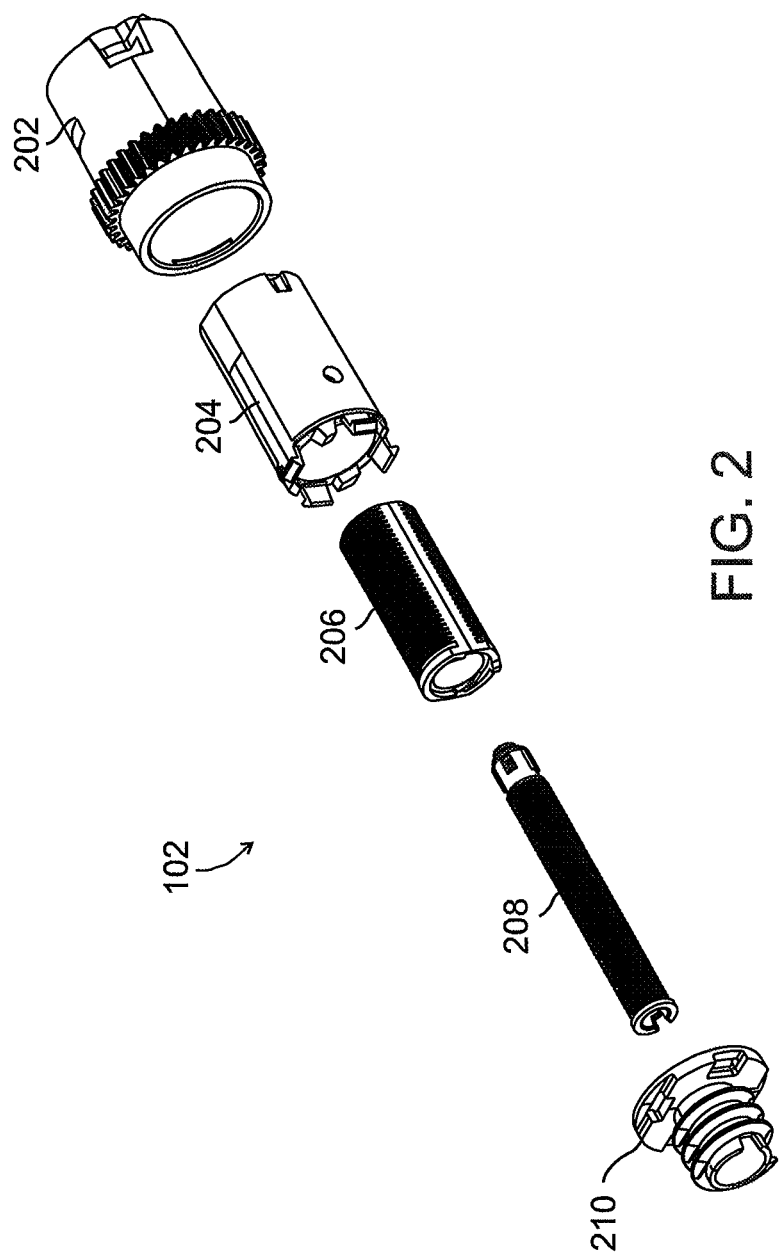
FIG. 2 is an exploded perspective view of an assembly of a drug delivery system, in accordance with an exemplary embodiment of the invention.

FIG. 2 illustrates an exploded perspective view of a telescoping assembly 102 of a drug delivery system 100, in accordance with an exemplary embodiment of the invention. In an embodiment of the invention, at least one component 104 includes a mid-screw 206, an internal screw 208, a driving element 106, for example a cartridge gear 202, a pushing element 108, for example a pushing nut screw 204 and/or a pushing element/nut cover 210. In an embodiment of the invention, at least two of the components are threaded and/or nested together and linear motion is achieved by a screwing motion between the threaded components. In an embodiment of the invention, the threading operatively connecting the components together is not continuous. In an embodiment of the invention, the pushing nut cover 210 is attached to a plunger or stopper in the cartridge of the patch injector. In an embodiment of the invention, the number of components 104 and/or the order of the components in the telescoping assembly 102 is varied, for example in reverse.

In some exemplary embodiments of the invention, at least a portion of the telescoping assembly 102 is configured to secure the telescoping assembly 102 for transport. The telescoping assembly 102 is configured to secure for transport by providing at least some resistance to unintended extension of the telescoping assembly 102, in an exemplary embodiment of the invention.

In an embodiment of the invention, for at least a first few threads of the internal screw 208, the mid screw 206 and/or pushing nut screw 204 of the telescoping assembly have not yet encountered resistance due to exerting force on the pushing nut cover 210 which is in contact with the fluidized portion of the cartridge. In some embodiments resistance may be delayed until telescoping assembly 102 fills a "gap". For example a gap 402 may occur between pushing nut screw 104 and pushing nut cover 110 as can be seen in more detail for example in FIGS. 4 and 5. Optionally, it is within this gap 402 that the telescoping assembly 102 is configured with a resistance element to provide resistance against unintended movement. Optionally, the torque required to overcome this resistance may be less than the nominal operative torque required to stall the driving motor. In an exemplary embodiment of the invention, this type of design configuration allows for securing the telescoping assembly 102 during transport without having to make any change or modification to the motor which powers it and it also avoids adding the torque of overcoming the securing resistance to the fluid flow resistance of pushing the fluid out of the cartridge and into the patient.

In some embodiments a "gap" may be behind cartridge gear 202. For example, when telescoping assembly begins to expand the rear end of cartridge gear 202 may be free to move backwards slightly until it fills the gap and is restrained. Movement of pushing nut cover 210 and associated resistance to movement of telescoping assembly 102 may be delayed until cartridge gear 202 fills the gap. Alternatively or additionally there be play in and/or in between elements which delay resistance to expansion of telescoping assembly 102.

Figure 3:
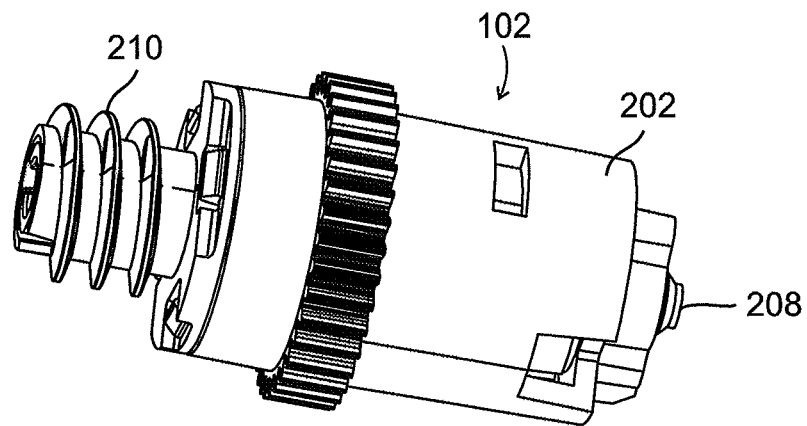
FIG. 3 is a perspective view of a closed assembly of a drug delivery system, in accordance with an exemplary embodiment of the invention.

FIG. 3 is a perspective view of a telescoping assembly 102 of a drug delivery system that is fully closed, a typical configuration for transport in accordance with an exemplary embodiment of the invention.

Figure 4:
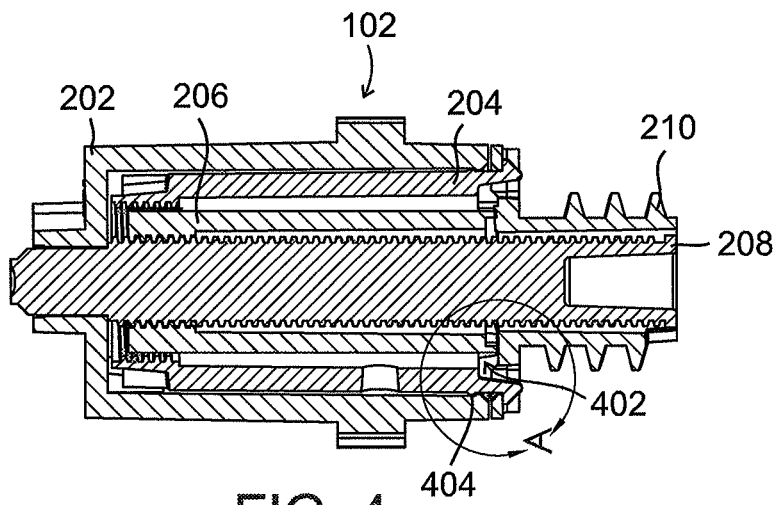
FIG. 4 is across-sectional view of the closed assembly of FIG. 3, in accordance with an exemplary embodiment of the invention.

FIG. 4 is a cross-sectional view of the closed telescoping assembly 102 of FIG. 3, in accordance with an exemplary embodiment of the invention. In order to provide resistance to unintended extension of the telescoping assembly 102, in some embodiments of the invention the pushing nut screw 204 is provided with a resistance element, for example an annular ring 404, shown and described in more detail with respect to FIGS. 5 and 6. The annular ring 404 is designed to catch on a lip 502 of the cartridge gear 202, shown and described in more detail in FIG. 5, during the first few rotations of the internal screw 208 (prior to the engagement of the mid screw 206 and/or the pushing nut screw 204 with the pushing nut cover 210). As used in this application, the annular ring 404 and the lip 502 are individually and collectively resistance elements.

Figure 5:
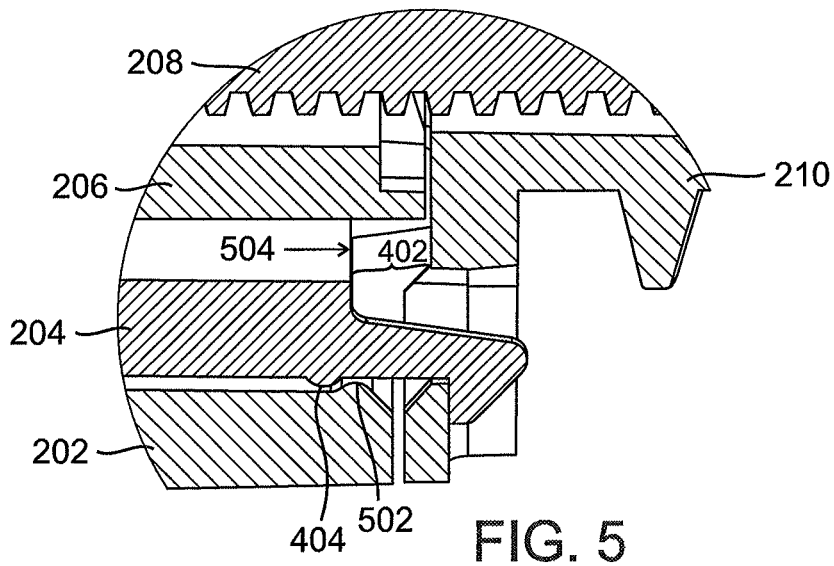
FIG. 5 is a close-up, cross-sectional view of a portion of the closed assembly of FIG. 4, in accordance with an exemplary embodiment of the invention.

FIG. 5 is a close-up, cross-sectional view of a portion of the closed telescoping assembly of FIG. 4, in accordance with an exemplary embodiment of the invention. In an exemplary embodiment of the invention, as the internal screw 208 twists to extend the telescoping assembly 102, mid screw 206 and pushing nut screw 204 to move in direction 504 towards the pushing nut cover 210, exerting force on the sloped contact surface of the annular ring 404 against the sloped contact surface of the lip 502. In an embodiment of the invention, the continuation of torque eventually overcomes the resistance between the annular ring 404 against the lip 502, allowing pushing nut screw 204 together with pushing nut cover 210 to move in direction 504 with less resistance by the rotational of internal screw 208.

In some embodiments of the invention, as the annular ring 404 passes over the lip 502, the cartridge gear 202 expands outward slightly from the longitudinal central axis of the assembly 102. Additionally or alternatively, in an embodiment of the invention, the pushing nut screw 204 deflects inward as the annular ring 404 passes over the lip 502. Additionally or alternatively, in an embodiment of the invention, the ring 404 and/or the lip 502 deform as the annular ring 404 passes over the lip 502. In some embodiments of the invention, the cartridge gear 202 expanding, the pushing nut screw 204 deflecting and/or the ring 404 and/or lip 502 deforming is elastic deformation. Optionally, it is plastic deformation. Optionally, there is a combination of elastic and plastic deformation. In some embodiments of the invention, there is no resistance and/or deformation induced in the telescoping assembly 102 during transport (prior to the annular ring 404 passing over the lip 502) and/or after the annular ring 404 passes over the lip 502 after the telescoping assembly 102 has been activated by the drug delivery system 100. In an embodiment of the invention, resistance and/or deformation occur for the short time that the annular ring 404 passes over the lip 502. In some embodiments of the invention, the ring 404 can pass over the lip 502 in the reverse direction, for example after use of the drug delivery system 100 by the patient. Optionally, a motor of the drug delivery system 100 drives the assembly 102 in reverse. Optionally, the patient or a caregiver manually drives the assembly 102 in reverse.

In some embodiments of the invention, the heights of the annular ring 404 and/or lip 502 are tailored to create a resistance which approximates the force required to push pushing nut screw cover 210 against the fluid in the cartridge. In some embodiments of the invention, the required torque to overcome the resistance provided by the annular ring 404 and the lip 502 is at least 50 gr-cm. Optionally, it is varied from 50-300 gr-cm. Optionally, the torque required is at least 100 gr-cm. Optionally, the torque required is varied from 100-250 gr-cm. The required torque level can be engineered in various ways, including using different materials, changing the diameters/thicknesses of the lip 502 and/or ring 404 and/or by altering the snap interference, in some embodiments of the invention. For example, in some embodiments, the snap interference may be between 0.01 and 1 mm.

In an exemplary embodiment of the invention, annular ring 404 extends around the entire outer circumference of the pushing nut screw 204, thereby spreading resistance over a "large" area. In an embodiment of the invention, by utilizing a substantial portion and/or the entire circumference of the pushing nut screw, partial manufacturing defects in portions of the ring and/or lip can be more easily overcome during nominal operation of the drug delivery system since resistance is spread over a wide area of the ring.

In some embodiments of the invention, the annular ring 404 extends around only a portion of the outer circumference of the pushing nut screw 204, thereby concentrating resistance over a "smaller" area, relative to the "large" embodiment described above. In some embodiments of the invention, a plurality of separate portions, each providing some resistance, form the "ring". For example, the plurality of separate portions could be individual teeth which provide resistance against a lip or lips or which set into an indentation or indentations. In an embodiment of the invention, the plurality of separate portions resist movement of one component of the telescoping assembly relative to a second component of the telescoping assembly.

In an embodiment of the invention, the lip 502 is located on the cartridge gear 202 to match the ring portion.

Figure 6:
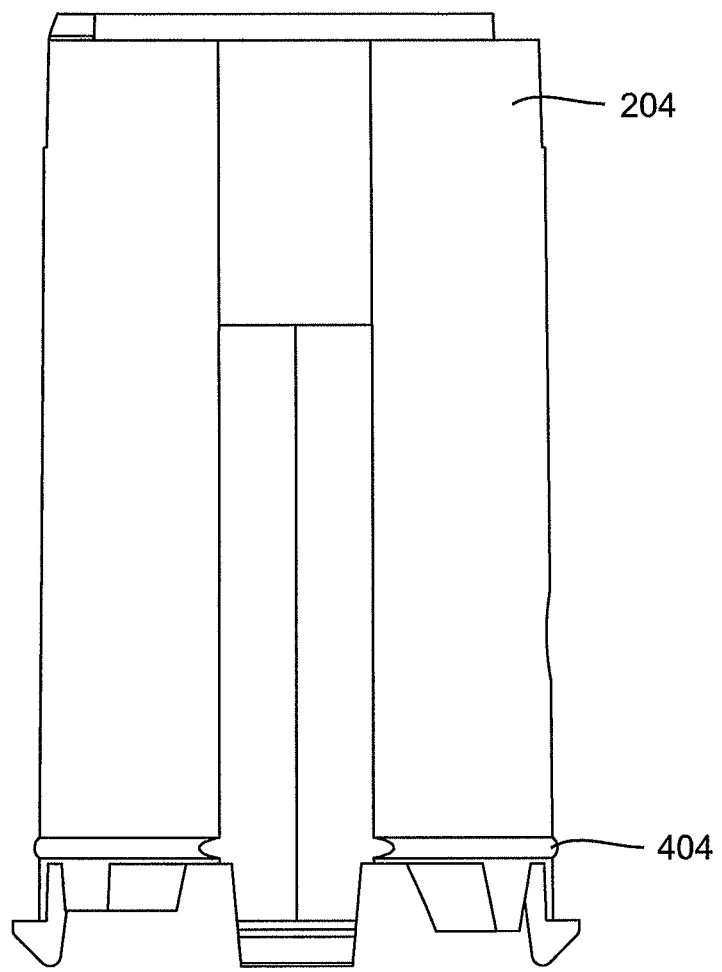
FIG. 6 is aside view of a pushing nut screw of an assembly of a drug delivery system, in accordance with an exemplary embodiment of the invention.

FIG. 6 is a side view of a pushing nut screw 204 of a telescoping assembly 102 of a drug delivery system 100, in accordance with an exemplary embodiment of the invention. Annular ring 404 is shown substantially extending around the out circumference of the pushing nut screw 204, in an exemplary embodiment of the invention.

In an additional and/or alternative and/or optional embodiment of the invention, telescoping assembly 102 is configured to resist unintended motion during transport by configuring the first few threads of the internal screw 208 in a way that increases friction. For example, the threads may be tighter and/or less deep and/or the shape of the screw 208 may not be perfectly round. As in other embodiments described herein, the higher friction threading (i.e. a resistance element) is found in the first few threads of the internal screw 208 before the mid screw 206 and pushing nut screw 204 are moved into a position to engage the pushing nut cover 210. In an embodiment of the invention, the closed transport configuration of the assembly is a configuration where the internal screw 208 before the mid screw 206 and pushing nut screw 204 have not yet been moved into a position to engage the pushing nut cover 210. This closed, transport configuration is in contrast to a nominal operative configuration, wherein the pushing nut cover 210 is supplied with operative force to advance the plunger in the drug delivery system to effectuate injection of a fluid pharmaceutical. Optionally, the pitch of the threading is varied.

Alternatively and/or additionally and/or optionally, the first few threads of the internal screw 208 are coated with an abrasive and/or adhesive material (i.e. a resistance element) which provides resistance to screwing, thereby securing telescoping assembly 102 for transport.

In an additional and/or alternative and/or optional embodiment of the invention, telescoping assembly 102 is configured to resist unintended motion during transport by providing a recess, a resistance element, in the pushing nut screw 204 which acts as a counterpart to lip 502, whereby when the lip 502 is positioned in the recess, linear movement of the telescoping assembly 102 is substantially or entirely prevented, securing the assembly 102 for transport.

In an additional and/or alternative and/or optional embodiment of the invention, telescoping assembly 102 is configured after manufacturing assembly to resist unintended motion during transport by crimping a portion of the cartridge gear 202 to temporarily impede motion of the pushing nut screw 204 until the motor of the drug delivery system 100 is activated thereby driving the pushing nut screw 204 through the crimp.

In an additional and/or alternative and/or optional embodiment of the invention, telescoping assembly 102 is configured after manufacturing assembly to resist unintended motion during transport by multiple interference elements. For example the resistance elements may include teeth that fit into indentations, for example in as illustrated in FIG. 10. Alternatively or additionally, the resistance element may include multiple sets of interfering projections.

In some embodiments of the invention, the required torque to overcome the resistance provided is at least 50 gr-cm. Optionally, it is varied from 50-300 gr-cm. Optionally, the torque required is at least 100 gr-cm. Optionally, the torque required is varied from 100-250 gr-cm. In an embodiment of the invention, such as any of those described herein, the resistance element provides sufficient resistance to ensure compliance under the ASTM D4169 performance testing of shipping containers and systems standards for combined air and rail transport. In some embodiments of the invention, the resistance element prevents unintended linear extension of the assembly while being subjected to extended vibrations up to 300 Hz. Optionally, extended vibration time is for hours, days or even weeks, for example in the case of cargo shipping overseas. In some embodiments of the invention, the resistance element prevents unintended linear extension of the assembly while being subjected to shocks up to 300 m/s2.

It should be understood that throughout the specification, where it is described that resistance is provided by a resistance element, for example by annular ring 404 and/or lip 502 and/or a recess, higher friction threading, abrasive/adhesive coatings, and/or crimping, the resistance that is provided is sufficient to prevent unintended extension of the telescoping assembly 102 during transport. In addition, it is also conceived that the resistance that is provided approximates the normal force required to inject the fluid in the cartridge into the patient (for example, in some embodiments the torque to overcome the resistance may ranging between 20% and 200% of the normal torque), or at the minimum is sufficient to prevent unintended extension of the telescoping assembly. It should also be understood that the "resistance element" can exist as an integral part of at least one of the components of the telescoping assembly 102 or exists independently of at least one of the components of the telescoping assembly 102. Further, at least one component of the assembly 102 can be configured with a resistance element during manufacturing, during assembly and/or after manufacturing and/or assembly. It should also be understood that various features described with respect to one embodiment of the invention are possibly applicable to other embodiments and that description of a feature with respect to one embodiment does not limit its application to only that embodiment.

Figure 7:
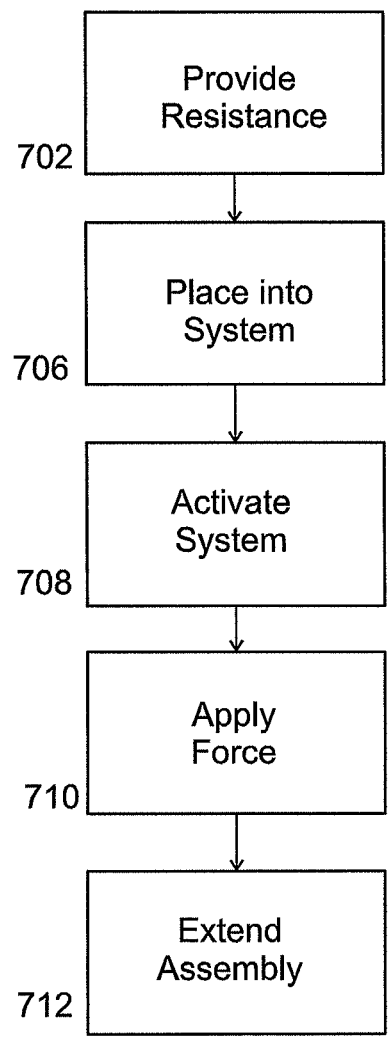
FIG. 7 is a flowchart of a method for using an assembly of a drug delivery system, in accordance with an exemplary embodiment of the invention.

FIG. 7 is a flowchart 700 of a method for using a telescoping assembly of a drug delivery system 100, in accordance with an exemplary embodiment of the invention. In an embodiment of the invention, resistance against extending is provided (702) to the telescoping assembly, such that the resistance prevents extension of the telescoping assembly as a result of vibrations encountered during transport but can be overcome by normal operation of the telescoping assembly and the drug delivery system in which it is placed (704), for example a patch injector like the SmartDose® Electronic Patch Injector System offered by Medimop Medical Projects Ltd., a subsidiary of West Pharmaceutical Services, Inc., or those described with respect to U. S. Pat. App. Publication No. 2009/0093792 and/or U.S. application Ser. No 13/521,181, the disclosures of which are incorporated herein by reference. The drug delivery system is activated (706), which applies (708) torque of nominal operation of the system and which is sufficient to overcome the provided (702) resistance while extending (710) the assembly to exert pressure on a fluid in a cartridge of the drug delivery system, in an embodiment of the invention.

Figure 8:
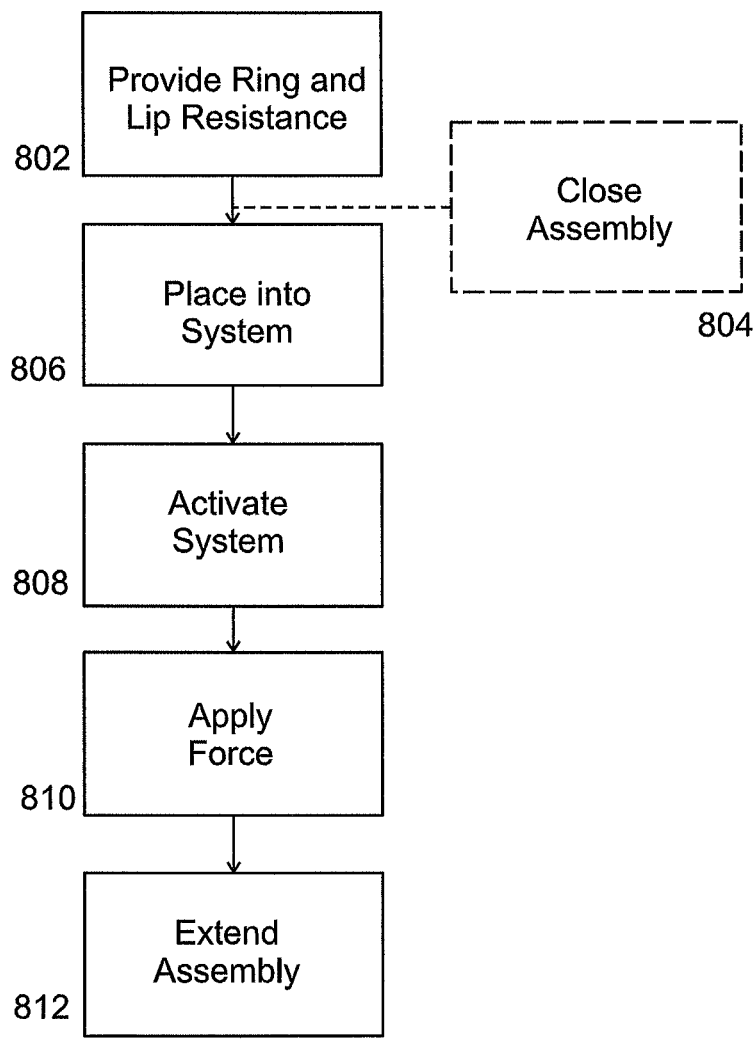
FIG. 8. is a flowchart of a method for using an assembly of a drug delivery system utilizing ring and lip resistance, in accordance with an exemplary embodiment of the invention.

FIG. 8 is a flowchart 800 of a method for using a telescoping assembly 102 of a drug delivery, system 100, in accordance with an exemplary embodiment of the invention. In an embodiment of the invention, at least one component of the telescoping assembly is provided (manufactured) with resistance (802) against extension of the telescoping assembly. In an embodiment of the invention, the telescoping assembly 102 is optionally closed (804) for transport after manufacturing. "Closed" means that the annular ring 404 on the pushing nut screw 204 of the telescoping assembly 102 is on the opposite side of a lip 502 on the cartridge gear 202 from the pushing nut cover 210. In some embodiments of the invention, the telescoping assembly 102 is manufactured in a closed configuration. The telescoping assembly 102, which is secured for transport as described herein, remains in a closed configuration and does not unintentionally extend during transport. The closed telescoping assembly 102 is placed (806) into a drug delivery system, for example a patch injector like the SmartDose® Electronic Patch Injector System offered by Medimop Medical Projects Ltd., a subsidiary of West Pharmaceutical Services, Inc. As the drug delivery system is activated (808), the resistance provided (802) within the first few twists of the internal screw 208 (and prior to contact of the mid screw 206 and/or pushing nut screw 204 with the pushing nut cover 210) via the annular ring 404 against the lip 502 is overcome. After continued torque applied (810) by the motor of the drug delivery system overcomes this resistance, in an embodiment of the invention, the eventual extension (812) of the telescoping assembly 102 and the injection of the fluid in a cartridge of the drug delivery system into a patient is enabled.

Figure 9:
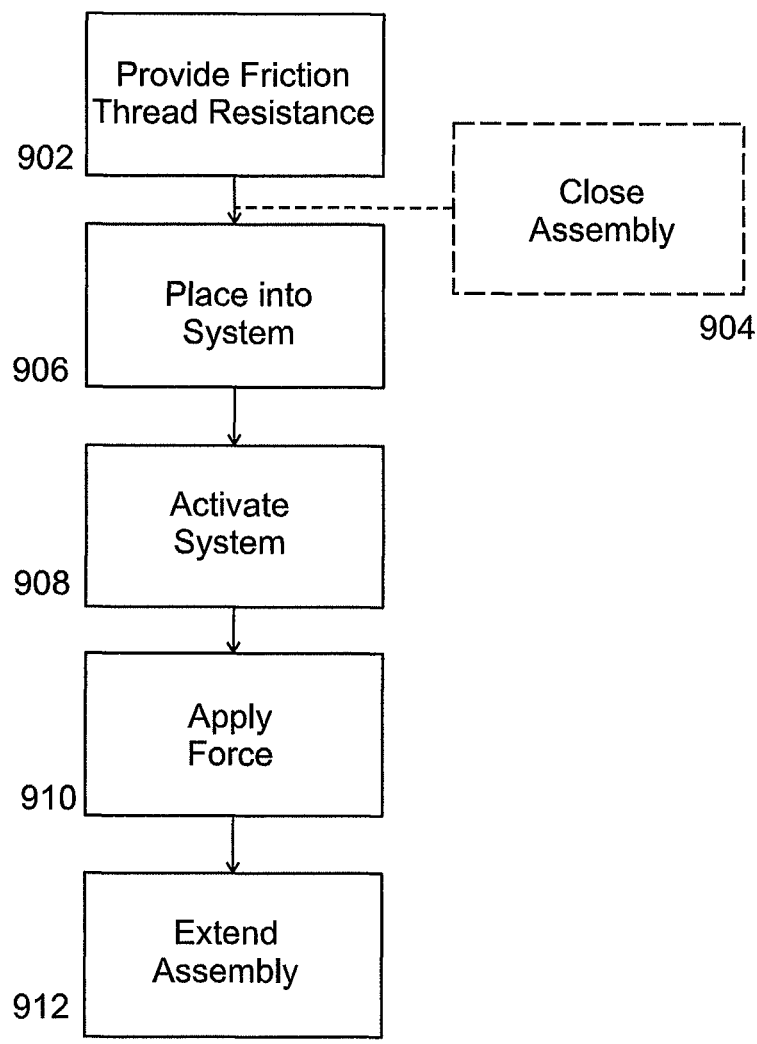
FIG. 9. is a flowchart of a method for using an assembly of a drug delivery system utilizing thread friction resistance, in accordance with an exemplary embodiment of the invention.

FIG. 9 is a flowchart 900 of an alternative method for using a telescoping assembly of a drug delivery system, in accordance with an exemplary embodiment of the invention. In an embodiment of the invention, at least one component of the telescoping assembly is provided (manufactured) with resistance (902) against extension of the telescoping assembly. In an embodiment of the invention, the telescoping assembly 102 is optionally closed (904) for transport after manufacturing. "Closed" in this embodiment means that the pushing nut screw 204 and the mid screw 206 are retracted away from the pushing nut cover 210, such as shown in FIG. 4, whereby there is gap 402 between the pushing nut screw 204, mid screw 206 and the pushing nut cover 210. In some embodiments of the invention, the telescoping assembly 102 is manufactured in a closed configuration. The telescoping assembly 102, which is secured for transport as described herein, remains in a closed configuration and does not unintentionally extend during transport. The closed telescoping assembly 102 is placed (906) into a drug delivery system, for example a patch injector like the SmartDose® Electronic Patch Injector System offered by Medimop Medical Projects Ltd., a subsidiary of West Pharmaceutical Services, Inc. As the drug delivery system is activated (908), the friction resistance provided (902) within the first few twists of the internal screw 208 (and prior to contact of the mid screw 206 and/or pushing nut screw 204 with the pushing nut cover 210) via higher friction threading of the internal screw 208 is overcome. In some embodiments of the invention, high friction threading is provided by configuring the first few threads of the internal screw 208 to be tighter and/or less deep and/or the shape of the screw 208 may not be perfectly round. After continued torque applied (910) by the motor of the drug delivery system overcomes this friction, in an embodiment of the invention, the eventual extension (912) of the telescoping assembly 102 and the injection of the fluid in a cartridge of the drug delivery system into a patient is enabled.

FIG. 10A illustrates an alternative exemplary embodiment of a cartridge gear 1004, a pushing nut screw 1002 and an inner screw 1008. In the exemplary embodiment, there are multiple interference elements between the top edge of the pushing nut screw and the bottom surface of the cartridge gear. For example protrusions (for example teeth 1032) on the top edge of pushing nut screw 1002 may fit into recess 1034 in cartridge gear 1004.

Optionally, on one side, teeth 1032 have a vertical wall 1036 (as shown for example in close up view FIG. 10B) that prevents over tightening of pushing nut screw 1032 to cartridge gear 1004 (which could cause thread lock). Optionally, on the other side of teeth 1032 has a sloped contact surface 1038. Optionally the slope of surface 1038 is greater than the pitch of the screw threads. Thus, when pushing nut screw 1002 is tightened to cartridge gear 1004, teeth 1032 enter recesses 1034 until walls 1036 contact the wall of the recesses, stopping further tightening. When the telescoping assembly is extended, first sloping surface 1038 provides a resistance to movement which when overcome allows extending of the assembly, distancing pushing nut screw 1002 from cartridge gear 1004 and ending the resistance. The use of multiple resistance elements may give an advantage the system resistance is not changed radically if one element is poorly manufactured and gives more or less resistance than intended.

It is expected that during the life of a patent maturing from this application many relevant motion resisting and/or securing technologies will be developed and the scope of the terms resisting and/or securing is intended to include all such new technologies a priori.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A telescoping assembly of a drug delivery system, comprising:
   a first component having a threaded member;
   a second component nested with the first component and threadedly linked with the threaded member of the first component, the second component being configured to move linearly with respect to the first component upon application of torque to one of the first and second components; and,
   a resistance element configured to resist linear movement during transport of the first component with respect to the second component in a closed transport configuration but which is adapted to be overcome during nominal operation of the drug delivery system, the resistance element including multiple interference elements forming a snap interference wherein one interference element snaps over another interference element to overcome the resistance to linear movement.

2. The telescoping assembly of claim 1, wherein the closed transport configuration is the state of the assembly before the linear movement of the second component with respect to the first component effectuates pumping in the drug delivery system.

3. The telescoping assembly of claim 1, wherein the second component further includes a pushing element and the first component further includes a drive element.

4. The telescoping assembly of claim 1, wherein the multiple interference elements comprise an annular ring and a counterpart lip.

5. The telescoping assembly of claim 4, wherein a pushing element is provided with the annular ring and a drive element is provided with the counterpart lip, which when the ring and the lip are forced together create the resistance to extension of the assembly.

6. The telescoping assembly of claim 1, wherein each interference element includes a tooth fitting into a recess.

7. The telescoping assembly of claim 1, wherein the torque required to overcome the resistance element is less than the nominal operative torque required to stall a driving motor of the drug delivery system.

8. The telescoping assembly of claim 1, wherein the required torque to overcome the resistance element is varied from 50-300 gr-cm.

9. The telescoping assembly of claim 1, wherein the resistance element is overcome by deformation of at least a portion of at least one of the first and second components.

10. The telescoping assembly of claim 9, wherein the deformation is at least one of elastic and plastic deformation.

11. The telescoping assembly of claim 1, wherein the resistance element includes a sloped contact surface.

* * * * *